US00PP24606P3

(12) United States Plant Patent
Brazelton et al.

(10) Patent No.: US PP24,606 P3
(45) Date of Patent: Jul. 8, 2014

(54) BLUEBERRY PLANT NAMED 'VENTURA'

(50) Latin Name: ***Vaccinium corymbosum* hybrid**
Varietal Denomination: Ventura

(75) Inventors: David M. Brazelton, Walterville, OR (US); Adam L. Wagner, Eugene, OR (US)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 162 days.

(21) Appl. No.: 13/385,910

(22) Filed: Mar. 12, 2012

(65) Prior Publication Data

US 2013/0239266 P1 Sep. 12, 2013

(51) Int. Cl.
*A01H 5/00* (2006.01)

(52) U.S. Cl.
USPC ..... Plt./157

(58) Field of Classification Search
CPC ..... A01H 5/08
USPC ..... Plt./157
See application file for complete search history.

(56) References Cited

U.S. PATENT DOCUMENTS

PP10,675 P 11/1998 Lyrene
PP16,404 P3 4/2006 Lyrene

*Primary Examiner* — June Hwu
(74) *Attorney, Agent, or Firm* — Davis Wright Tremaine LLP; Dale C. Hunt; Wenhua Yu

(57) ABSTRACT

The new blueberry plant variety 'Ventura' is provided. 'Ventura' is a commercial variety intended for the hand harvest fresh market. The variety is very vigorous, ripens early and produces a medium to large berry with excellent flavor. 'Ventura' has an estimated chilling requirement of approximately 300 to 500 hours.

3 Drawing Sheets

Latin name of the family, genus, and species:
Family—Ericaceae.
Genus—*Vaccinium.*
Species—*corymbosum* hybrid.
Variety denomination: The new blueberry plant claimed is of the variety denominated 'Ventura'.

CROSS REFERENCE TO RELATED APPLICATIONS

None.

STATEMENT REGARDING FEDERALLY-SPONSORED RESEARCH AND DEVELOPMENT

None.

BACKGROUND OF THE INVENTION

The present invention relates to the discovery of a new and distinct cultivar of southern highbush blueberry (*Vaccinium corymbosum* L. hybrid) plant, referred to as 'Ventura', also referred to as 'FF-89', as herein described and illustrated.

The new blueberry plant variety 'Ventura' was selected in Lowell, Oreg. in 2006. 'Ventura' is a commercial variety intended for the hand harvest fresh market. The variety is very vigorous, ripens early and produces a medium to large berry with excellent flavor. 'Ventura' has an estimated chilling requirement of approximately 300 to 500 hours.

Pedigree and History: The new blueberry plant originated from a cross made in 2000 of 'FL96-24' (pollen parent, unpatented) by 'FL00-60' (female parent, unpatented). The new blueberry plant variety 'Ventura' has been planted in replicated trials since 2007.

When compared to commercial variety 'Springhigh' (U.S. Plant Pat. No. 16,404), the new variety 'Ventura' ripens slightly sooner, is higher yielding, and has firmer fruit with lighter color.

When compared to commercial variety 'Star' (U.S. Plant Pat. No. 10,675), new variety 'Ventura' ripens approximately two weeks earlier, has higher yields, and lighter fruit color.

The new blueberry plant variety 'Ventura' has maintained its distinguishing characteristics throughout successive asexual propagations. The variety has been repeatedly asexually reproduced through softwood cuttings in Lowell, Oreg., and the clones are phenotypically identical to the original plant.

SUMMARY OF THE INVENTION

The new blueberry plant variety 'Ventura' has not been observed under all possible environmental conditions. The phenotype may vary somewhat with variations in environment and cultural practices such as temperature and light intensity without, however, any variance in genotype.

The following traits have been repeatedly observed in Lowell, Oreg. and are determined to be the unique characteristics of the new blueberry plant variety 'Ventura':

1. Vigorous Plant.
2. Excellent Flavor.

BRIEF DESCRIPTION OF THE DRAWINGS

The accompanying photographic illustration shows typical specimens in full color of the foliage and fruit of the new variety 'Ventura'. The colors are as nearly true as is reasonably possible in a color representation of this type.

BOTANICAL DESCRIPTION

Figure 1:
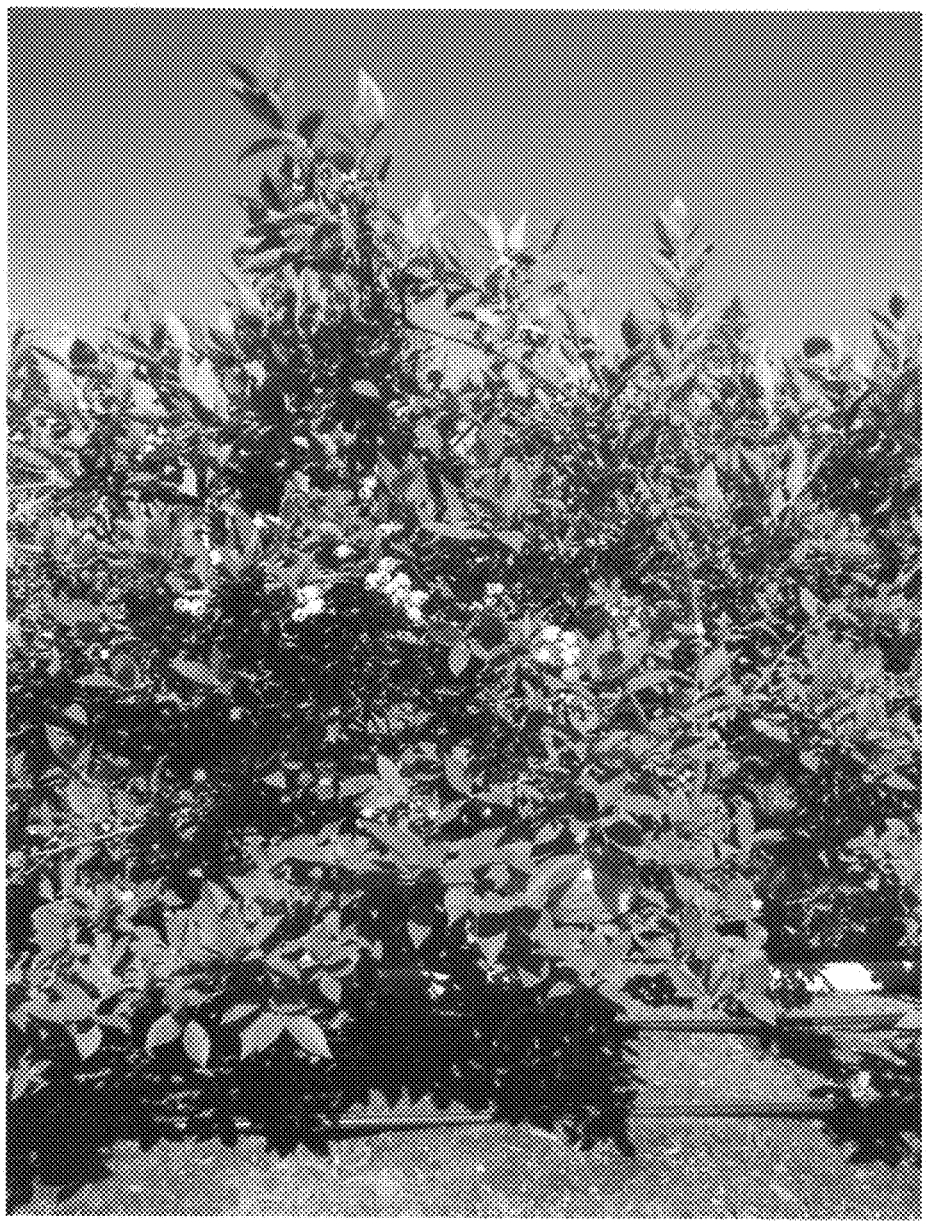
FIG. 1 is a photograph of the new variety 'Ventura', highlighting the plant's vigorous nature.
Figure 2:
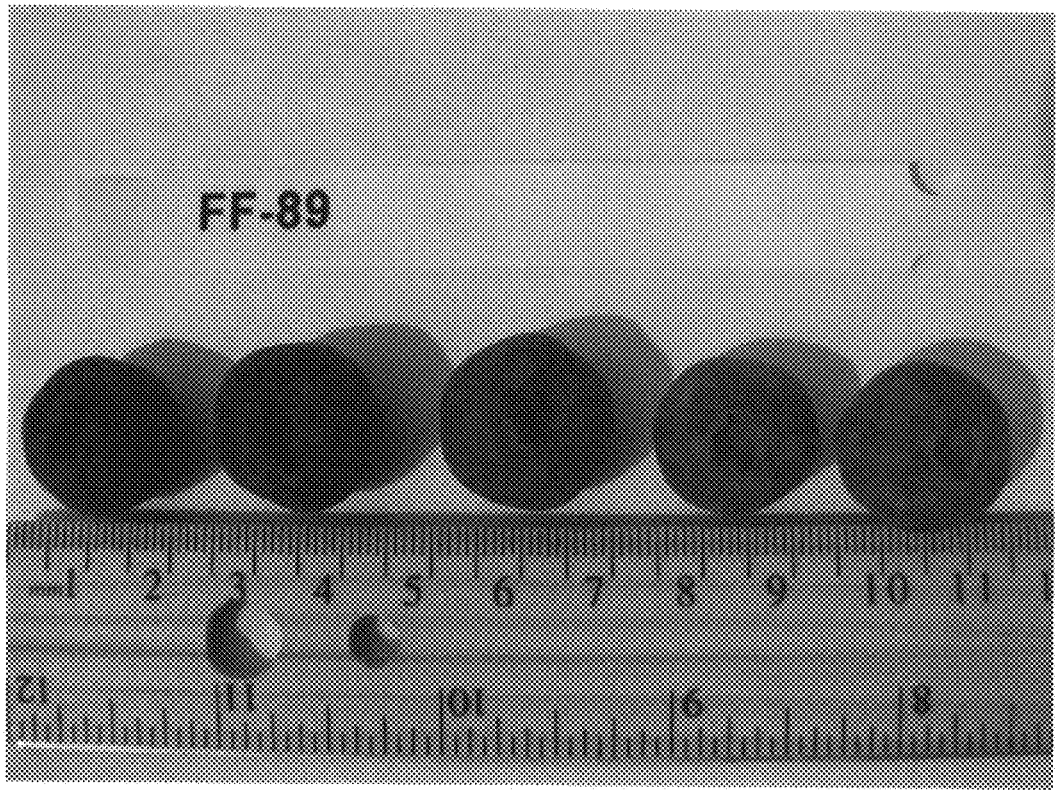
FIG. 2 is a photograph of the fruit of the new variety 'Ventura'.
Figure 3:
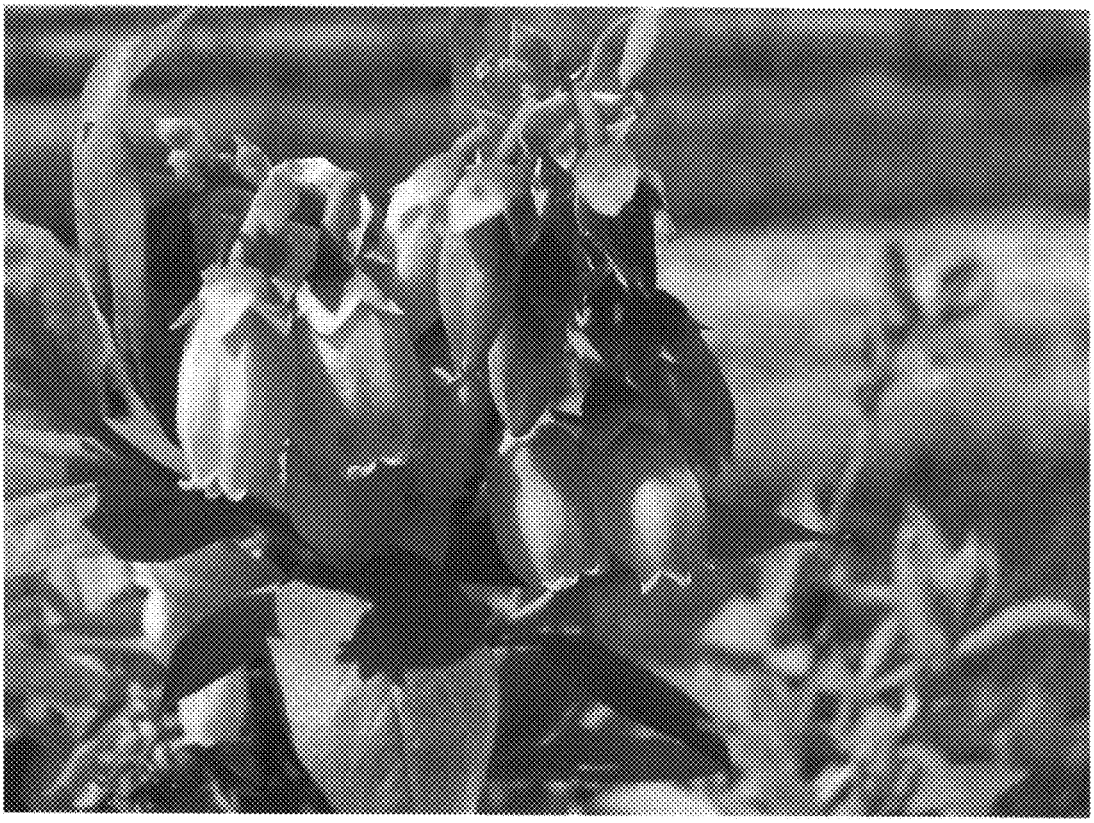
FIG. 3 is a photograph of the flowers of the new variety 'Ventura'.

The following detailed description sets forth the distinctive characteristics of 'Ventura'. The data which defines these characteristics was collected from asexual reproductions of the original selection. Dimensions, sizes, colors, and other characteristics are approximations and averages set forth as accurately as possible. The plant history was taken on plants approximately three years of age, and the descriptions relate to plants grown in the field in Lowell, Oreg. Descriptions of fruit characteristics were made on fruit grown in Delano, Calif. Color designations are from "The Pantone Book of Color" (by Leatrice Eiseman and Lawrence Herbery, Harry N. Abrams, Inc., Publishers, New York 1990). Where the Pantone color designations differ from the colors in the photographs, the Pantone colors are accurate.

Classification:
- *a. Family*.—Ericaceae.
- *b. Genus.—Vaccinium.*
- *c. Species.—Corymbosum* hybrid.
- *d. Common name*.—Southern Highbush Blueberry.

Parentage:
- *Female parent*.—FL00-60 (Unpatented).
- *Male parent*.—FL96-24 (Unpatented).

Market class: 'Ventura' is a commercial blueberry variety intended for the hand harvest fresh market.

PLANT

Plant size:
- a. *Height of plant*.—Average of 40" in Oregon (4 year old plants).
- *b. Canopy diameter*.—Average 30" in Oregon (4 year old plants).

Growth habit: Upright.
Plant vigor: Vigorous.
Twigginess: Low.
Suckering: Low.
Evergreenness: Evergreen in Oregon.
Chilling requirement: Approximately 300-500 hours at temperatures at or below 45° F. (about 7° C.).
Cold hardiness: USDA Hardiness zones 7-9.
Productivity: In Delano, Calif. on 3 year old plants, 13.78 lbs per plant harvested.
Propagation: Easy to propagate from softwood cuttings.
Disease and pest resistance/susceptibility:
- *a. Phytophthora*.—Does not appear to be overly susceptible.
- *b. Stem blight*.—Undetermined.
- *c. Cane canker*.—Undetermined.
- *d. Leaf spot*.—Does not appear to be overly susceptible.
- *e. Bud mites*.—Undetermined.
- *f. Disease survival*.—Good.

TRUNK AND BRANCHES

Texture:
- *a. Surface texture new wood*.—Smooth.
- *b. Surface texture* 1 *year wood*.—Smooth.
- *c. Surface texture* 3 *years and older wood*.—Rough.

Color:
- *a. Color new wood*.—Pantone Oasis 16-0540.
- *b. Color rough bark at* 1 *year*.—Pantone Moss 16-0532 and Redwood 18-1443.
- *c. Color rough bark at* 3 *years and older*.—Pantone Brush 16-1317, Smoke Gray 14-1209, and Acorn 18-1314.

FOLIAGE

Internode length: Average of 13.58 mm.
Leaf dimensions:
- *a. Leaf length*.—Average of 71.81 mm.
- *b. Leaf width*.—Average of 37.86 mm.

Leaf shape: Elliptical with acute apex and base.
Leaf margin: Entire.
Leaf color upper leaf surface:
- *a. Mature leaves*.—Pantone Artichoke green 18-0125.
- *b. New leaves*.—Pantone Herbal Garden 15-0336, and Tabasco 18-1536.

Leaf color lower leaf surface: Pantone Grasshopper 18-0332.
Fall leaf color: Pantone Mineral 17-1537.
Pubescence:
- *a. Pubescence upper leaf surface*.—Absent.
- *b. Pubescence lower leaf surface*.—Absent.
- *c. Pubescence leaf margins*.—Absent.

Precocity: New vegetative growth before flowering in Lowell, Oreg.
Leaf petiole:
- *a. Petiole length*.—Average of 2.66 mm.
- *b. Petiole surface texture*.—Smooth.
- *c. Petiole color*.—Pantone Lettuce Green 13-0324.

FLOWERS

Flower arrangement: Compound raceme. Clusters arranged alternately along branches.
Flower shape: Cylindrical to slightly urceolate.
Fragrance: Sweet, faint.
Flower bud density: Medium.
Flower length: Average of 13.14 mm.
Immature flower color: Pantone Holly Berry 17-1633 and Pastel Parchment 11-0603.
Flowering period: February through May in Lowell, Oreg.
Flowering cluster: Loose.
Number flowers: Average of 3-5 flowers per cluster in Lowell, Oreg.
Stigma location: Average of 0.5 mm below the lip of the corolla.
Corolla:
- *a. Corolla length*.—Large flowers, Average of 10.22 mm.
- *b. Corolla diameter*.—Average of 10.698 mm.
- c. *Corolla color*.—Pantone Snow White 11-0602.
- *d. Corolla texture*.—Smooth.
- *e. Corolla aperture*.—Average of 5.29 mm.

Flower peduncle:

a. *Peduncle length flower*.—Variable, with an average of 9.87 mm.

b. *Peduncle color*.—Pantone Green Oasis 15-0538.

Flower pedicel:

a. *Pedicel length flower*.—Average of 14.7 mm.

Calyx:

a. *Calyx diameter*.—Average of 5.42 mm.

b. *Calyx surface*.—Smooth.

c. *Calyx color*.—Pantone Green Oasis 15-0538, Peridot 17-0336 and Lilas 16-1708.

Style length: Average of 8.58 mm.

Pistil color: Pantone Green Olive 17-0535.

Anther:

a. *Anther length*.—Average of 4.36 mm.

b. *Anther color*.—Pantone Leather Brown 18-1142.

Pollen:

a. *Pollen staining*.—95% fertile, staining with 2% aceto-carmine stain.

b. *Pollen abundance*.—Medium.

c. *Pollen color*.—Pantone Cornsilk 13-0932.

Self compatibility: Good, 73% of self pollinated flowers reaching maturity.

Average of size of the inflorescence: 37.7 mm.

FRUIT

Mean harvest date first pick: May 3 in Delano, Calif.

Mean date last pick: May 31 in Delano, Calif.

Calyx:

a. *Calyx aperture*.—Average of 5.47 mm.

b. *Calyx lobes*.—Five lobes on larger berries, which are not well defined. The smaller berries are more rounded.

c. *Calyx depth*.—Average of 2.63 mm.

Berry cluster: Loose.

Berry pedicel:

a. *Length*.—Average of 9.68 mm.

b. *Surface texture*.—Smooth.

Berry peduncle:

a. *Length*.—Variable, average of 11.4 mm.

b. *Surface texture*.—Smooth.

Berries per cluster: 3 to 4.

Berry detachment: Moderately easy.

Berry weight: Average of 2 g.

Berry height: Average of 12.5 mm.

Berry width: Average of 16.22 mm.

Berry shape: Round to slightly teardrop shaped (rhomboid), with a rounded shoulder.

Berry color:

a. *Immature berry color*.—Pantone Mellow Green 12-0426 and Holly Berry 17-1633.

b. *Berry skin color on plant*.—Pantone Dapple Grey 16-3907.

c. *Berry skin color after harvest*.—Pantone Dapple Gray 16-3907 and Patriot Blue 19-3925.

d. *Berry skin color after polishing*.—Pantone Dark Navy 19-4013.

Berry wax: Persistent wax, moderate amount.

Berry flesh Color: Pantone Pastel Yellow 11-0616.

Pedicel scar: Average of 2.22 mm.

Berry firmness: Firm.

Berry flavor: Sweet and fruity.

Berry texture: Moderately firm.

SEED

Seed color: Pantone Madder Brown 19-1331.

Seed length: Average of 1.81 mm.

Seed width: Average of 1.14 mm.

Seed weight: Average of 0.4 mg.

Seeds per berry: Average of 14 Seeds per Berry.

DISTINGUISHING FEATURES FROM PARENTS

TABLE 1

| Name of paternal parent | Characteristic(s) in which the candidate variety differs from the paternal parent | Describe the expression of the characteristic for the maternal parent | Describe the expression of the characteristic for 'Ventura' |
|---|---|---|---|
| F196-24 | Looseness of fruit in the cluster | Medium loose | Loose |
| F196-24 | Anthocyanin coloration of the corolla tube | Medium | weak |
| F196-24 | Fruit firmness | Very firm | medium |

TABLE 2

| Name of maternal parent | Characteristic(s) in which the candidate variety differs from the maternal parent | Describe the expression of the characteristic for the maternal parent | Describe the expression of the characteristic for 'Ventura' |
|---|---|---|---|
| FL00-60 | Length of corolla tube | Medium | Long |
| FL00-60 | Fruit firmness | Very firm | medium |
| FL00-60 | Fruit size | Medium | large |

The invention claimed is:

1. A new and distinct variety of blueberry plant named 'Ventura', substantially as illustrated and described herein.

* * * * *